US00PP12322P2

(12) United States Plant Patent
Walden

(10) Patent No.: US PP12,322 P2
(45) Date of Patent: Jan. 1, 2002

(54) MINIATURE ROSE PLANT NAMED 'JACORG'

(75) Inventor: John K. Walden, Burlington, WA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,214

(22) Filed: Dec. 6, 1999

(51) Int. Cl.[7] ..... A01H 5/00
(52) U.S. Cl. ..... Plt./116
(58) Field of Search ..... Plt./116, 121, 119

*Primary Examiner*—Howard J. Locker
(74) *Attorney, Agent, or Firm*—Klarquist Sparkman, LLP

(57) ABSTRACT

A miniature rose plant having dwarf plant habit; pointed ovoid buds that open to high centered, two inch, copper-orange flowers; and dark green, glossy, disease resistant foliage.

1 Drawing Sheet

The present invention relates to a new and distinct variety of rose plant of the miniature class which was originated by me by crossing an unnamed seedling, with the variety SAValife (U.S. Plant Pat. No. 5,482).

The primary objective of this breeding was to produce a new rose variety having a dwarf plant habit, two inch open flowers, novel, orange flower color, pointed ovoid buds that open to a high centered flower, and dark green, glossy, disease resistant foliage on a plant suitable for growing in outdoor gardens. The objective was substantially achieved, along with other desirable improvements, as evidenced by the following unique combination of characteristics that are outstanding in the new variety and that distinguish it from its parents, as well as from all other varieties of which I am aware:

1. A dwarf, miniature rose habit (16 to 18 inches tall);
2. Two inch, novel, copper orange flowers, blending to pink with age;
3. Pointed ovoid buds that open with a moderately high center;
4. Dark green, glossy foliage that resists powdery mildew and rust; and
5. Moderately vigorous growth in outdoor gardens.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unnamed seedling× unnamd seedling).

*Pollen parent.*—SAValife (U.S. Plant Pat. No. 5,482).

Classification:

*Botanical.*—*Rosa hybrida.*

*Commercial.*—Miniature rose.

FLOWER

Observations made in September, 1999, from specimens grown in a garden environment at Somis, Calif.

Blooming habit: Recurrent.

Bud:

*Size.*—⅝ to ¾ inch long when the petals start to unfurl.

*Form.*—The bud form is short, pointed ovoid.

*Color.*—When sepals first divide, bud color is near Red Group 42A. When half blown, the upper sides of the petals are Orange Group 24A with tinting of Orange Group 25A near petal edges; and the lower sides of the petals are near Orange-Red Group 30A.

*Sepals.*—Color: Yellow-Green Group 144A and Greyed-Red Group 178A on edges. Surface texture: Hairy. There are three normally appendaged sepals. There are two unappendaged sepals with hairy edges.

*Receptacle.*—Color: Yellow-Green Group 144B with some bronzing of Greyed-Red Group 178A. Shape: Funnel. Size: Small (about ¼ inch×5/16 inch). Surface: Hairy.

*Peduncle.*—Length: Short, averaging about 1⅛ inches. Surface: Hairy. Color: Between Yellow-Green Group 144A and Yellow-Green Group 144B, with bronzing of Greyed-Red Group 178A. Strength: Stiff; erect.

Bloom:

*Size.*—Small. Average open size is about two inches.

*Borne.*—Singly and several together in pyramidal clusters of three to seven blooms.

*Stems.*—Strength: Normal. Average length is about six to eight inches.

*Form.*—When first open: Bloom is high centered. Permanence: Flattens; outer petal edges curl slightly.

*Petalage.*—Number of petals under normal conditions: 20–25.

*Color.*—The upper sides of the petals are Yellow-Orange Group 23B with a blush of Red Group 37A at and near the petal edge. The reverse sides of the petals are a blend of Yellow-Orange Group 23B and Red Group 37A giving a darker appearance near Orange-Red Group 33C. The base of each petal has a ¼ inch flare of Yellow Group 7A, that often radiates up the midvein of the petal. The major color on the upper side is Yellow-Orange Group 23B.

*Variegations.*—None.

*Discoloration.*—The general tonality at the end of the first day: Yellow-Orange Group 23B. At the end of the third day: A lightening toward Red Group 38A. With further aging, color finishes near Orange Group 27C before petals drop.

*Fragrance.*—Slight; spicy.

Petals:

*Texture.*—Thin, leathery.

*Shape.*—Pointed; deltoid.

*Form.*—Tips slightly recurved.

*Arrangement.*—Imbricated (regularly arranged). Petaloids in the center are many (three to eight); large.

*Persistence.*—Petals drop off cleanly before drying.

*Lastingness.*—On the plant: Long (about eight to nine days). As a cut flower: Not tested.

Reproductive parts:

*Anthers.*—Size: Medium. Quantity: Many. Color: White Group 155A. Arrangement: Regular around styles.

*Filaments.*—Color: Near Yellow Group 13B.

*Pollen.*—Color: Near Yellow-Orange Group 17A.

*Styles.*—Color: Near Red Group 53B at top; Green-White Group 157D at bottom.

*Stigmas.*—Color: Near Green-White Group 157B.

Plant:

*Form.*—Bush.

*Growth.*—Vigorous; dwarf; upright; branching. At maturity, height is 16 to 18 inches, width is 16 to 20 inches.

Foliage: Number of leaflets on normal mid-stem leaves: Five; often seven.

*Size.*—Small (3¼ to 3½ long×1⅝ to 2 inches wide).

*Quantity.*—Normal.

*Color.*—New foliage: Upper surfaces: New Greyed-Purple Group 183A. Lower surfaces: Near Greyed-Purple Group 183B. Old foliage: Upper surface: Near Yellow-Green Group 147A. Lower surface: Green Group 138B.

Leaflets:

*Shape.*—Broadly oval.

*Texture.*—Glossy; smooth.

*Edge.*—Serrated.

*Serration.*—Single.

*Petiole rachis.*—Color: Greyed-Purple Group 183A (new); Yellow-Green Group 147B (old).

*Petiole underside.*—With prickles.

*Stipules.*—Medium (about ½ inch); lightly bearded.

*Disease resistance.*—Resistant to mildew and rust; susceptible to blackspot under normal growing conditions.

Wood:

*New wood.*—Color: Greyed-Purple Group 184A. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Medium (5/16 to ⅜ inch); straight and angled downward.

*Color when young.*—Greyed-Red Group 181A.

*Color when mature.*—Between Greyed-Yellow Group 161B and Greyed-Yellow Group 161C.

Small prickles:

*Quantity.*—On main stalks: None. On laterals: None.

I claim:

1. A new and distinct variety of rose plant of the miniature class, substantially as herein shown and described, characterized particularly by its dwarf plant habit; pointed ovoid buds that open to high centered, two inch, copper-orange flowers; and dark green, glossy, disease resistant foliage.

* * * * *

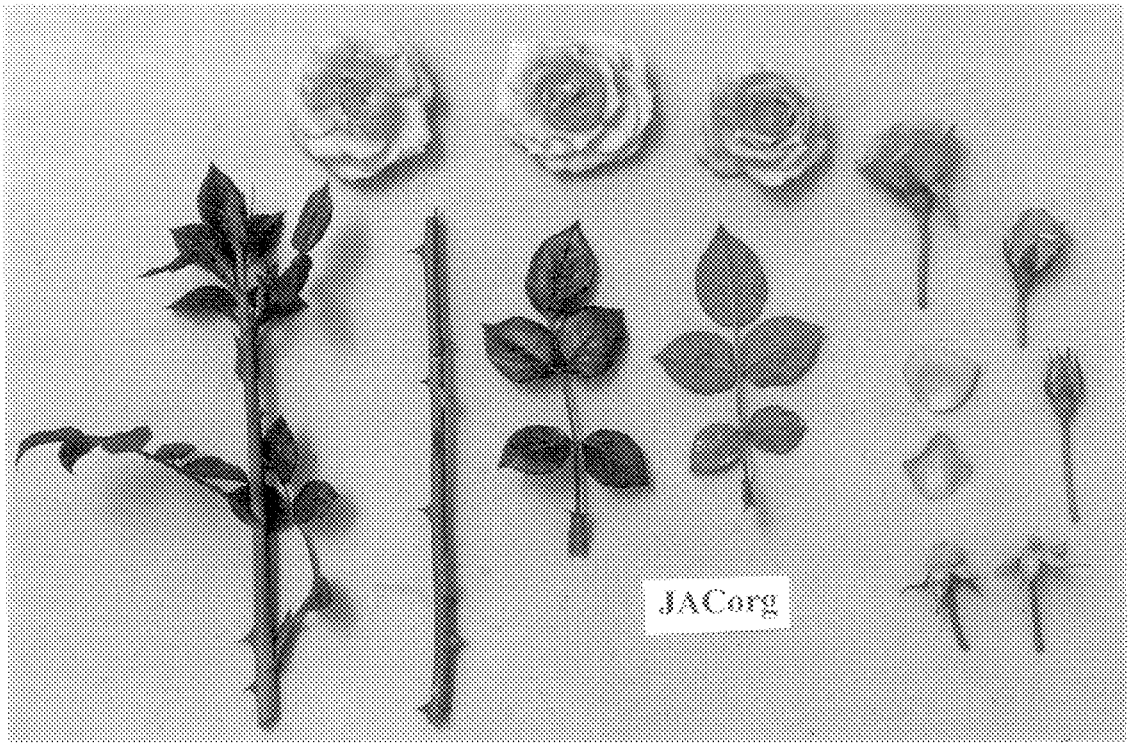
JACorg